United States Patent [19]

Grinstead et al.

[11] 4,123,435
[45] Oct. 31, 1978

[54] NITRO-SUBSTITUTED BENZOXAZOLES HAVING UTILITY AS METALLURGICAL EXTRACTANTS

[75] Inventors: Robert R. Grinstead; Kenneth C. Jones, both of Walnut Creek; Wilmonte A. Nasutavicus, Lafayette, all of Calif.

[73] Assignee: The Dow Chemical Company, Midland, Mich.

[21] Appl. No.: 827,650

[22] Filed: Aug. 25, 1977

[51] Int. Cl.² ............................................. C07D 263/56
[52] U.S. Cl. ................................ 260/307 D; 423/24; 423/DIG. 14
[58] Field of Search ................................. 260/307 D

[56] References Cited
U.S. PATENT DOCUMENTS

| | | | |
|---|---|---|---|
| 3,655,347 | 4/1972 | Mattison et al. | 23/312 |
| 4,020,081 | 4/1977 | Mackay et al. | 260/307 D |

*Primary Examiner*—Raymond V. Rush

[57] ABSTRACT

Nitro-substituted 2-(2-hydroxyphenyl)benzoxazoles of the formula

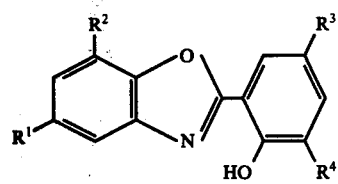

wherein one of $R^3$ and $R^4$ is $-NO_2$ and the other is $-H$, $-NO_2$ or alkyl of 1 to 20 carbons and $R^1$ and $R^2$ independently are $-H$ or alkyl of 1 to 20 carbons, with the proviso that $R^1$, $R^2$, $R^3$ and $R^4$ contain a total of at least 7 carbons, are acidic, oil soluble compounds having utility for extraction of copper from strongly acidic ore leaches. Excellent selectivity for copper over iron is exhibited by the subject compounds.

7 Claims, No Drawings

NITRO-SUBSTITUTED BENZOXAZOLES HAVING UTILITY AS METALLURGICAL EXTRACTANTS

BACKGROUND OF THE INVENTION

The decreasing availability of high grade copper ores necessitates utilization of lower grade ores, which often contain substantial amounts of iron. A processing method which promises to become important for recovery of copper from such ores comprises acid-leaching, liquid/liquid extraction and acid stripping. However, in order for this method to be economic for copper ores which yield acid leaches of high iron content, it is necessary to employ extractants which are highly selective for copper over iron.

U.S. Pat. No. 4,020,081 discloses that 2-(2-hydroxyphenyl)-benzoxazoles of the formula

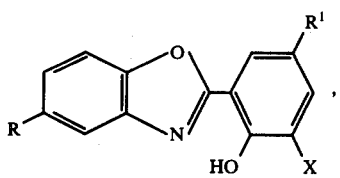

wherein R is H or alkyl of 1 to 20 carbons, $R^1$ is H, Cl or alkyl of 1 to 20 carbon atoms, X is H or Cl and at least one of R and $R^1$ must contain 6 or more carbons, have utility for extraction of copper (and other metal values) from ammoniacal aqueous solutions having pH's of from about 7 to about 10.5.

The patent infers that the disclosed compounds will extract metal values from other types of aqueous solutions but is silent as to specifics in this regard. Leaches having pH's in the latter range will not contain significant amounts of iron and selectivity for copper over iron is not required of the disclosed compounds.

In the course of a search for compounds which would selectively extract copper from unneutralized acid leaches, several benzoxazoles of the preceding formula were independently conceived, made and tested by the present inventors. The results were disappointing; the extent and/or rate of copper extraction (or stripping) was too low or poor selectivity for copper over iron was found. However, the compounds were otherwise well suited for the intended purpose and the possibility of improving their performance by introducing various types of substituents in the prototype 2-(2-hydroxyphenyl) benzoxazole molecule was considered.

To be suitable for practical use as an extractant, a candidate compound must simultaneously satisfy a minimum of eight different requirements (which are familiar to those skilled in the art; see column 1 of the '081 patent). This poses a problem, in that a change in composition intended to make the compound more suitable in one respect may also make it less suitable in another respect. Thus, for example, a modification which increases the ability of the compound to take up copper ions at a pH of about 2 may adversely effect solubility properties and/or unduly increase acid requirements for stripping.

OBJECTS OF THE INVENTION

The general object of the present invention is to provide a novel group of benzoxazoles which are suitable for the extractive recovery of copper (and other metal values) from acidic ore leaches.

A more particular object is to provide such compounds which are selective extractants for copper over iron at pH's of from about 1.5 to about 2.5, but can be stripped with dilute mineral acids.

A further object is to provide a method of recovering copper from unneutralized acid leaches of copper ores containing substantial amounts of iron.

Still other objects will be made apparent to those skilled in the art by the following disclosure and claims.

SUMMARY OF THE INVENTION

The present invention is a group of hydrocarbyl- and nitro-substituted benzoxazoles and their use as extractants for metal values dissolved in acidic ore leaches.

The compounds of the invention are those of the formula

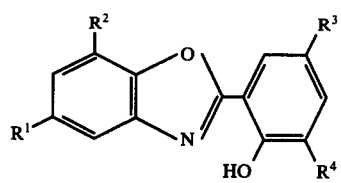

wherein one of $R^3$ and $R^4$ is $-NO_2$ and the other is $-H$, $-NO_2$ or alkyl of 1 to 20 carbons and $R^1$ and $R^2$ independently are $-H$ or alkyl of 1 to 20 carbons, with the proviso that $R^1$, $R^2$, $R^3$ and $R^4$ contain a total of at least 7 carbons.

Those compounds of the invention wherein $R^1$–$R^4$ contain at least 8 carbons have better oil solubility and accordingly are preferred. This is particularly the case when $R^3$ and $R^4$ are both nitro groups. In the latter circumstance, the total number of carbons in $R^1$ and $R^2$ preferably is at least 12.

The method of the invention comprises:
(1) contacting an aqueous, acidic copper solution, having a pH of from about 1.5 to about 2.5, with a solution of a compound of the preceding formula in a waterimmiscible liquid, thereby forming a solution in said liquid of a chelate of said copper and said compound;
(2) separating the latter solution from the resulting copper-depleted aqueous solution;
(3) stripping the chelate-containing liquid by contacting it with a dilute aqueous mineral acid having a pH of about 1.3 or less, thereby disrupting said chelate and transferring the copper therefrom to said acid; and
(4) separating the copper loaded stripping acid from the stripped extractant solution and recovering the copper content of the loaded acid.

DETAILED DESCRIPTION

Preparation of the Benzoxazoles

The benzoxazoles of the present invention are conveniently prepared by oxidative ring closure of corresponding Schiff bases of the formula

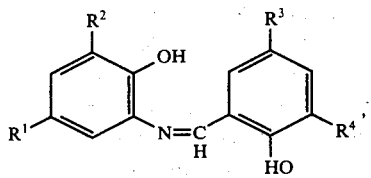

wherein $R^1$–$R^4$ are as defined in the preceding summary. The Schiff base intermediates in turn are readily prepared according to well known procedures by condensation of corresponding o-hydroxyanilines and salicylaldehydes.

A variety of oxidants may be employed to oxidize the Schiff bases to the benzoxazoles by the procedure of: F. F. Stephens and J. D. Bower, The Preparation of Benziminazoles and Benzoxazoles From Schiff Bases; Parts I & II; J. Chem. Soc., 2971 (1949) and 1722 (1950). Such oxidants include lead tetraacetate, chloranil and benzoyl peroxide.

The aminophenol starting materials for the Schiff bases can be made in good yields by a two-step method. In the first step, a phenol having $R^1$ and $R^2$ substituents (as defined above) in the para and ortho positions respectively, is reacted with bromine or chlorine in carbon tetrachloride solution. The resulting orthohalo phenol is then reacted with ammonia (as liquid ammonia or as a solution of $NH_3$ or $NH_4OH$ is a solvent such as "glyme" (ethylene glycol diethyl ether)) under autogeneous pressure at a temperature ranging from about 125° C. (for replacement of —Br by —$NH_2$) to about 230° C. (for replacement of —Cl), for a period of from about 4 to about 24 hours.

The nitro-substituted salicylaldehyde starting materials can be made by nitration of the corresponding 2-hydroxybenzaldehydes (unsubstituted or substituted ortho or para to the hydroxyl group with an alkyl group of 1 to 20 carbons). The nitration is effected with nitric acid (25% to fuming) in glacial acetic acid at a temperature below 20° C. (The alkyl substituted salicylaldehyde precursors may be made by known methods.)

The method of benzoxazole preparation disclosed in U.S. Pat. No. 4,020,081 involves the condensation of salicylamides with aminophenols at temperatures of about 200°–240° C. and may also be used to make benzoxazoles of the present invention.

Use of the Benzoxazoles

The nitro-substituted benzoxazoles of the invention are employed in a conventional manner for extraction of copper (and other metal values, such as nickel, zinc, etc.) from acidic ore leaches. One or more of the subject benzoxazoles is dissolved in an otherwise suitable, water-immiscible liquid and the solution is intimately contacted with the leach. The phases are allowed to disengage and are then separated. Ordinarily, the metal content of the loaded extractant solution is recovered by a conventional procedure comprising stripping the solution with a dilute aqueous mineral acid, such as about 0.1 normal hydrochloric or sulfuric acid. The solution and the acid are intimately contacted, disengaged and separated from each other. The loaded strip is then processed in a conventional manner, such as by electrolysis, to recover the metal (Cu° for example).

The water-immiscible liquid in which the benzoxazole is dissolved will usually be an organic hydrocarbon or chlorocarbon solvent, such as kerosene, xylene, methylene chloride, carbon tetrachloride, perchloroethylene, and the like. However, any otherwise suitable extraction medium which is capable of dissolving enough of the benzoxazole to form an at least 0.02 molar solution may be employed.

The phase ratio for the aqueous and "organic" phases can vary widely but ratios outside of the range of from about 20:1 to about 1:20 volumes of extractant solution per volume of leach will generally be impractical and ratios within the range of from about 5:1 to about 1:5 are preferred.

When the ore leach contains any substantial amount of iron (or similarly behaving metals), the overall operation of extracting and stripping must effect a considerable decrease in the ratio of copper (etc.) to iron. However, a substantial increase in copper concentration in the strip (as compared to the leach) must also be realized if the operation is to be practical. Accordingly, the volume ratio of stripping acid to loaded organic must be held within relatively narrow limits and the phase ratio for the stripping step will usually be within the range of from about 1:10 to about 10:1 and, preferably, about 1:10 to about 1:1.

Such expedients as staged, countercurrent contacting of aqueous and organic phases, continuous operation and stripping acid recycle are familiar to those skilled in the art and are viable options in the practice of the present invention.

EXAMPLES

The following examples are for purposes of illustration and are not to be construed as limiting the scope of the invention to an extent inconsistent with the claims appended to this specification.

EXAMPLE 1 — Preparation of 2-(2-hydroxy-5-nitrophenyl)-5-nonylbenzoxazole (I)

To a 300 ml round-bottomed, three-neck flask equipped with a resin-coated, magnetic stirring bar, a reflux condenser fitted with a $CaCl_2$ drying tube, and a thermometer, was added 30 ml. of acetic acid and 20 ml of acetic anhydride. The solution was heated to 55° C. and stirred while 3.43 grams (5 m moles) of $Pb_3O_4$ was added in small portions over a period of an hour (final temperature 65° C.). The resulting lead tetracetate solution was cooled to room temperature and 1.92 grams (5 m moles) of the Schiff base corresponding to the title compound was added in small portions, with stirring, over a period of 0.5 hour. The reaction mixture was stirred at room temperature for 2 hours and poured into 300 ml of cold water. The resulting mixture was extracted with 80 ml of diethyl ether and the extract was washed with seven 50 ml portions of water, one 50 ml portion of saturated aqueous NaCl, dried over anhydrous $Na_2SO_4$ and stripped of solvent in a rotary evaporator under reduced pressure to a final kettle conditions of 35° C. at 0.3 mm Hg (after 18 hours). The residue was a viscous oil (1.9 grams; 99% of theory) which was identified as the title compound (M — 382.46) by NMR (nuclear magnetic resonance) analysis: 1.0 (m, 19H, $CH_3CH_2$), 8.2 (m, 6H, ArH ). (ArH means Aryl hydrogen.)

EXAMPLE 2

The following benzoxazoles were prepared from the corresponding Schiff bases by the method of the preceding example:

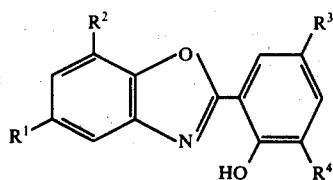

| Compound | R¹ | R² | R³ | R⁴ | NMR Analysis (δ ppm) and Molecular Weight |
|---|---|---|---|---|---|
| II | Nonyl | H | H | NO₂ | 1.1 (m, 19H, CH₃, CH₂) <br> 8.0 (m, 6H, ArH). <br> M = 382.46 |
| III | H | H | Nonyl | NO₂ | 1.2 (m, 19H, CH₃, CH₂) <br> 7.7 (m, 4H, ArH) <br> 8.3 (m, 2H, ArH) <br> M = 382.46 |
| IV | Dodecyl | H | NO₂ | H | 1.0 (m, CH₂, CH₃) <br> 8.0 (m, ArH <br> M = 424.55 |
| V | Dodecyl | H | H | NO₂ | 1.0 (m, 25H, CH₃, CH₂) <br> 8.0 (m, 6H, ArH) <br> M = 424.55 |
| VII | t-Butyl | H | t-Butyl | NO₂ | 1.4 (S, 18H, (CH₃)₃C—) <br> 7.5–8.5 (m, 5H, ArH <br> 12.9 (S, 1H, ArOH) <br> M = 368.43 |
| XII | Dodecyl | H | NO₂ | NO₂ | 0.5 –2.0 (m, 25H, CH₃, CH₂) <br> 7.0 –9.5 (m, 5H, ArH) |

| Compound | R¹ | R² | R³ | R⁴ | NMR Analysis (δ ppm) and Molecular Weight |
|---|---|---|---|---|---|
| IX | t-Butyl | t-Butyl | t-Butyl | NO₂ | 1.5 (d, 27H, (CH₃)₃C—) <br> 7.7 (m, 2H, ArH) <br> 8.3 (m, 2H, ArH) <br> M = 424.55 |
| X | t-Butyl | t-Butyl | Nonyl | NO₂ | 0.5–2.0 (m, 37H, CH₃, CH₂) <br> 7.5–8.5 (m, 4H, ArH) <br> M = 494.68 |
| XI | t-Butyl | t-Butyl | Nonyl | Cl | 0.5–2.0 (m, 37H, CH₃, CH₂) <br> 7.2–8.2 (m, 4H, ArH) <br> M = 484.13 |

(Compound XI is not a compound of the present invention. It closely resembles a compound of U.S. Pat. No. 4,020,081 and is included herein for purposes of comparison only.)

EXAMPLE 3—Preparation of 2-(2-hydroxy-3-nitrophenyl)-5,7-di-t-butylbenzoxazole (VI)

To a 300 ml round-bottomed flask equipped with a magnetic stirring bar and a reflux condenser was added 2.955 grams (8 m moles) of the Schiff base corresponding to the title compound, 1.94 grams (8 m moles) of benzoyl peroxide and 50 ml of CHCl₃. The resulting solution was stirred and refluxed for two hours. TLC (Thin Layer Chromatographic) analysis (on silica gel; eluted with EtOAc/Benzene, ¼) showed the reaction was completed. The solvent was removed under reduced pressure and the residual solid dissolved in 60 ml of DMF (dimethyl formamide). 16.1 ml of 0.9936 M NaOH was added with swirling and the reaction mixture was diluted with 80 ml of water. The solution was then extracted three times with diethyl ether (150 ml, 50 ml and 50 ml) and the combined extracts were washed and dried as in Example 1. The ether was stripped off in a rotary evaporator, under reduced pressure, at a kettle temperature of 40° C. The residue was obtained as 2.89 grams (98% of theory) of a pale yellow solid which melted at 148°–150° C. and was identified as the title compound by elemental analysis:

Calcd. for C₂₁H₂₄N₂O₄: C, 68.5; H, 6.5; N, 7.9. Found: C, 68.3; H, 6.5; N, 7.6.

EXAMPLE 4

The following benzoxazoles were prepared by the preceding method (Example 3). (Refer to the formula in Example 2.)

EXAMPLE 5 — Preparation of 2-(2-hydroxy-3-nitro-5-nonylphenyl)-5-t-butylbenzoxazole (VIII)

To a 300 ml round-bottom two-necked flask equipped with a Teflon-coated magnetic stirring bar and a Dean-Stark water separator were added 5-nonyl-3-nitrosalicylaldehyde (2.93g, 10 m moles), 4-t-butyl-2-aminophenol (1.65g, 10 m moles), and benzene (50 ml). The reaction solution was refluxed with water separation for 1.75 hours; TLC analysis (EtOAc/φH, ¼) showed the reaction to be complete.

The stirring solution was cooled and to it was added benzoyl peroxide (2.42g, 10 m moles); the solution was then refluxed for one hour. (TLC analysis showed complete disappearance of starting materials after only 5 minutes reflux.) The solvent was removed at reduced pressure, followed by dissolution of the reaction mixture in DMF (30 ml). To the swirling solution was added 20.13 ml of 0.9936 N NaOH (20.00 m moles NaOH) followed by water (80 ml). The reaction mixture was then extracted twice with diethyl ether (100 ml, 50 ml), and the combined organic layer extracted with water (12 × 50 ml), saturated aqueous NaCl (1 × 50 ml), dried over anhydrous Na$_2$SO$_4$ (5 min), filtered, and the solvent removed over a period of 2.5 hours at reduced pressure in a rotary evaporator; final conditions 0.3 mm, 85° C., to give 4.15 g (95%) of dark solid product which was identified as the title compound by NMR; 0.5-2.0 (m, 28H, CH$_3$, CH$_2$).

EXAMPLE 6 — Selective Copper Extraction

Reagent grade metal sulfate salts and sulfuric acid were used to prepare an aqueous stock solution (synthetic "leach") that contained about 0.8 gram/liter each of cupric copper and ferric iron at a pH of 2. Ten milliliter aliquots of this stock solution were pipetted into several small bottles and two ml. of either dilute sulfuric acid, water, or dilute sodium carbonate solution were added to give a final aqueous volume of 12 ml. and an initial pH in the range of 1.7 to 2.7. Four ml of an approximately 0.1 molar solution of the subject benzoxazole in toluene were then pipetted into all but one ("feed") of the sample bottles which were then placed on a mechanical shaker and vigorously mixed for 30 minutes. The two phases were carefully separated, the equilibrium pH of the aqueous phase was measured, and the copper and iron concentrations of the aqueous phase determined by atomic absorption spectrometry. The percent of metal extracted under these conditions was calculated from the difference between the feed and (equilibrium) aqueous raffinate concentrations, as follows:

$$\% \text{ Extracted} = \left(1 - \frac{C_{Aqueous}}{C_{Feed}}\right) \times 100,$$

C being the concentration of the metal in the phase indicated.

Table I summarizes the results obtained by the preceding test method, at each of several pH's, with eleven different benzoxazoles representative of those of the present invention.

For purposes of comparison, data are also given for a benzoxazole (Compound XI) which is a homolog of one disclosed in U.S. Pat. No. 4,020,081, in which — according to the radical definitions employed herein — R$^1$ and R$^2$ are t-butyl, R$^3$ is nonyl and R$^4$ is chloro (rather than nitro).

TABLE I
SELECTIVE EXTRACTION OF COPPER FROM SYNTHETIC LEACH BY BENZOXAZOLES OF THE FORMULA, 0.1 MOLAR IN TOLUENE.

| (Compound) | | | | | | Concentration of metal in aqueous phase, ppm[1] | | % metal in feed extracted | |
|---|---|---|---|---|---|---|---|---|---|
| R$^1$ | R$^2$ | R$^3$ | R$^4$ | Sample | pH | Cu$^{2+}$ | Fe$^{3+}$ | Cu$^{2+}$ | Fe$^{3+}$ |
| Nonyl | H | NO$_2$ | H | Feed | 2.10 | 871 | 800 | — | — |
| (Compound I) | | | | 1 | 1.62 | 712 | 800 | 18 | 0 |
| | | | | 2 | 1.92 | 596 | 800 | 32 | 0 |
| Nonyl | H | H | NO$_2$ | Feed | 2.14 | 856 | 783 | — | — |
| (II) | | | | 1 | 1.64 | 689 | 783 | 20 | 0 |
| | | | | 2 | 1.95 | 594 | 783 | 31 | 0 |
| H | H | Nonyl | NO$_2$ | Feed | 2.17 | 842 | 783 | — | — |
| (III) | | | | 1 | 1.66 | 653 | 783 | 22 | 0 |
| | | | | 2 | 1.96 | 555 | 783 | 34 | 0 |
| | | | | 3 | 2.27 | 499 | 759 | 41 | 3 |
| Dodecyl | H | NO$_2$ | H | Feed | 2.09 | 871 | 800 | — | — |
| (IV) | | | | 1 | 1.67 | 871 | 800 | 0 | 0 |
| | | | | 2 | 2.04 | 754 | 800 | 13 | 0 |
| Dodecyl | H | H | NO$_2$ | Feed | 2.09 | 871 | 800 | — | — |
| (V) | | | | 1 | 1.62 | 767 | 800 | 12 | 0 |
| | | | | 2 | 1.91 | 585 | 800 | 33 | 0 |
| t-Butyl | t-Butyl | H | NO$_2$ | Feed | 2.14 | 856 | 783 | — | — |
| (VI) | | | | 1 | 1.53 | 476 | 783 | 44 | 0 |
| | | | | 2 | 1.79 | 312 | 783 | 64 | 0 |
| t-Butyl | H | t-Butyl | NO$_2$ | Feed | 2.16 | 829 | 785 | — | — |
| (VII)[2] | | | | 1 | 1.67 | 658 | 785 | 21 | 0 |
| | | | | 2 | 1.94 | 523 | 785 | 37 | 0 |
| | | | | 3 | 2.22 | 433 | 776 | 48 | 1 |
| t-Butyl | H | Nonyl | NO$_2$ | Feed | 2.18 | 838 | 768 | — | — |
| (VIII) | | | | 1 | 1.64 | 574 | 764 | 32 | 1 |
| | | | | 2 | 1.92 | 405 | 730 | 52 | 5 |
| | | | | 3 | 2.19 | 302 | 764 | 64 | 1 |
| t-Butyl | t-Butyl | t-Butyl | NO$_2$ | Feed | 2.17 | 842 | 783 | — | — |
| (IX) | | | | 1 | 1.65 | 520 | 783 | 38 | 0 |
| | | | | 2 | 1.87 | 351 | 779 | 58 | 0 |
| | | | | 3 | 2.08 | 240 | 783 | 71 | 0 |
| t-Butyl | t-Butyl | Nonyl | NO$_2$ | Feed | 2.17 | 878 | 659 | — | — |
| (X) | | | | 1 | 1.69 | 644 | 632 | 27 | 4 |
| | | | | 2 | 1.96 | 525 | 643 | 40 | 2 |
| | | | | 3 | 2.18 | 457 | 651 | 48 | 1 |
| t-Butyl | t-Butyl | Nonyl | Cl | Feed | 2.17 | 878 | 659 | — | — |
| (XI)[3] | | | | 1 | 1.68 | 827 | 625 | 6 | 5 |
| | | | | 2 | 2.05 | 815 | 651 | 7 | 1 |
| | | | | 3 | 2.31 | 804 | 613 | 8 | 7 |
| Dodecyl | H | NO$_2$ | NO$_2$ | Feed | 2.17 | 863 | 775 | — | — |
| (XII)[4] | | | | 1 | 1.67 | 657 | 737 | 24 | 5 |

TABLE I-continued
SELECTIVE EXTRACTION OF COPPER FROM SYNTHETIC LEACH BY BENZOXAZOLES OF THE FORMULA 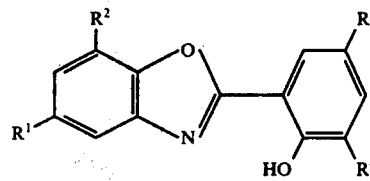 , 0.1 MOLAR IN TOLUENE.

| (Compound) | | | | | | Concentration of metal in aqueous phase, ppm[1] | | % metal in feed extracted | |
|---|---|---|---|---|---|---|---|---|---|
| $R^1$ | $R^2$ | $R^3$ | $R^4$ | Sample | pH | $Cu^{2+}$ | $Fe^{3+}$ | $Cu^{2+}$ | $Fe^{3+}$ |
| | | | | 2 | 1.99 | 636 | 765 | 26 | 1 |

NOTES:
[1] Parts per million.
[2] 0.06 molar in toluene.
[3] Representative of prior art extractants; not part of present invention.
[4] 0.024 normal in toluene.

The data of the preceding Table illustrates single-contact copper recoveries of up to 71% and copper to iron selectivities ranging from 5/1 to ∞ (no detectable iron extraction) by use of the subject extractants with ore leaches having pH's of from about 1.5 to about 2.3.

Comparison of the results for compounds X and XI shows a substantial improvement in both copper recovery and selectivity over iron upon replacement of the chlorine substituent in compound XI (representative of prior art extractants) with a nitro group, according to the present invention.

Those benzoxazoles of the present invention in which $R^3$ is H or alkyl and $R^4$ is a nitro group are considered to be the most effective extractants for copper. It is evident from the Table that the specific compounds of this type numbered as III, V, VII and IX are particularly effective, the latter three compounds being of superior selectivity.

It is apparent from the effect of pH on the percent of the copper in the feed which is extracted that retention of the copper in the aqueous phase is favored at lower pH's. That is, if the loaded organic phase is contacted with aqueous acid having a pH of about 1.3 or less, it will be essentially stripped of its copper content.

We claim:

1. A benzoxazole of the formula wherein:
one of $R^3$ and $R^4$ is $NO_2$ and the other is H, $NO_2$ or alkyl of 1 to 20 carbons, and
$R^1$ and $R^2$ independently are H or alkyl of 1-20 carbons,
with the proviso that $R^1$, $R^2$, $R^3$ and $R^4$ contain a total of at least 7 carbons.

2. A compound as defined in claim 1 wherein $R^1$, $R^2$, $R^3$ and $R^4$ contain at least 8 carbons.

3. A compound as defined in claim 1 wherein $R^3$ and $R^4$ are both —$NO_2$ groups and $R^1$ and $R^2$ contain a total of at least 12 carbons.

4. A compound of claim 2 in which each of $R^1$ and $R^2$ is an alkyl group of 4 or more carbons.

5. A compound of claim 2 wherein $R^3$ is H or alkyl and $R^4$ is $NO_2$.

6. The compound of claim 5 in which each of $R^1$, $R^2$ is a t-butyl group, $R^3$ is H and $R^4$ is $NO_2$.

7. The compound of claim 2 in which each of $R^1$, $R^2$ and $R^3$ is t-butyl and $R^4$ is $NO_2$.

* * * * *